United States Patent [19]
Roizman

[11] Patent Number: 5,714,153
[45] Date of Patent: *Feb. 3, 1998

[54] METHOD OF INDUCING ANTIBODY PRODUCTION AGAINST AN INFECTIOUS AGENT IN A HOST

[75] Inventor: Bernard Roizman, Chicago, Ill.

[73] Assignee: Arch Development Corporation, Chicago, Ill.

[*] Notice: The term of this patent shall not extend beyond the expiration date of Pat. No. 5,641,651.

[21] Appl. No.: 681,811

[22] Filed: Jul. 29, 1996

Related U.S. Application Data

[63] Continuation of Ser. No. 332,467, Oct. 31, 1994, Pat. No. 5,641,651, which is a continuation of Ser. No. 996,961, Dec. 23, 1992, abandoned.

[51] Int. Cl.$^6$ .................. A61K 39/245; C12N 15/86
[52] U.S. Cl. .................. 424/231.1; 424/93.2; 424/93.6
[58] Field of Search .................. 435/69.1, 172.1, 435/172.3, 240.2, 320.1, 325; 424/199.1, 204.1, 229.1, 231.1, 93.2, 93.6

[56] References Cited

U.S. PATENT DOCUMENTS 4,859,587  8/1989  Roizman .................. 424/199.1

FOREIGN PATENT DOCUMENTS 176170     4/1986  European Pat. Off. .
WO 92/04050 3/1992  WIPO .

OTHER PUBLICATIONS

Arsenakis et al., "Evaluation of Isogenic Viral Promoters for Expression of Foreign Genes in Herpes Simplex Virus I Genomes," Methods in Molecular and Cellular Biology, vol. 2, pp. 5–16 (1990).

Banks et al., "Vaccination with the Immediate–Early Protein ICP47 of Herpes Simplex Virus–Type I (HSV–1) Induces Virus–Specific Lymphoproliferation, but Fails to Protect Against Lethal Challenge," Virology, vol. 200, pp. 236–245 (1994).

Honess et al., "Regulation of Herpesvirus Macromolecular Synthesis," Journal of Virology, pp. 8–19 (Jul. 1974).

Honess et al., "Regulation of Herpesvirus Macromolecular Synthesis: Sequential Transition of Polypeptide Synthesis Requires Functional Viral Polypeptides," Proc. Nat. Acad. Sci., vol. 72, No. 4, pp. 1276–1280 (Apr. 1975).

Hummel et al., "Herpes Simplex Virus Expressing Epstein–Barr Virus Nuclear Antigen 1," Virology, vol. 148, pp. 337–348 (1986).

Mackem et al., "Structural Features of the Herpes Simplex Virus α Gene 4, 0, and 27 Promoter–Regulatory Sequences Which Confer α Confer α Regulation on Chimeric Thymidine Kinase Genes," Journal of Virology, vol. 44, No. 3, pp. 939–949 (Dec. 1982).

McGeoch et al., "Complete DNA Sequence of the Long Unique Region in the Genome of Herpes Simplex Virus Type 1," J. Gen. Virol., vol. 69, pp. 1531–1574 (1988).

McGeoch et al., "Sequence Determination and Genetic Content of the Short Unique Region in the Genome of the Herpes Simplex Virus Type 1," J. Mol. Biol., vol. 181, pp. 1–13 (1985).

Meigner et al., "In Vivo Behavior of Genetically Engineered Herpes Simplex Viruses R7017 and R7020. II. Studies in Immunocompetent and Immunosuppressed Owl Monkeys (*Aotus trivirgaus*)," The Journal of Infectious Diseases, vol. 162, pp. 313–321 (1990).

Meigner et al., "In Vivo Behavior of Genetically Engineered Herpes Simplex Viruses R7017 and R7020: Construction and Evaluation in Rodents," The Journal of Infectious Diseases, vol. 158, No. 3, pp. 602–614 (Sep. 1988).

Post et al., "Chicken Ovalbumin Gene Fused to a Herpes Simplex Virus α Promoter and Linked to a Thymidine Kinase Gene is Regulated Like a Viral Gene," Molecular and Cellular Biology, pp. 233–240 (Mar. 1982).

Post et al., "Cloning Reiterated and Nonreiterated Herpes Simplex Virus 1 Sequences as BamHI Fragments," Proc. Natl. Acad. Sci., vol. 77, No. 7, pp. 4201–4205 (Jul. 1980).

Post et al., "Regulation of α Genes of Herpes Simplex Virus: Expression of Chimeric Genes Produced by Fusion of Thymidine Kinase With α Gene Promoters," Cell, vol. 24, pp. 555–565 (May 1981).

Shih et al., "Expression of Hepatitis B Virus S Gene by Herpes Simplex Virus Type 1 Vectors Carrying α–and β–regulated Gene Chimeras," Proc. Natl. Acad. Sci. vol. 81, pp. 5867–5870 (Sep. 1984).

Wagner et al., "Individually HSV Transcripts," The Herpes Viruses, vol. 3, Chapter 2, pp. 45–104 (1984).

Whitley et al., "Vaccines Against Herpes Simplex Infections," New Generation Vaccines, pp. 825–841 (1990).

*Primary Examiner*—David Guzo
*Attorney, Agent, or Firm*—Marshall, O'Toole, Gerstein, Murray & Borun

[57] ABSTRACT

The present invention relates to synthetic herpes simplex virus (HSV) promoters which are constructed by operatively linking the 5' nontranscribed domain of an HSV α gene to a fragment containing the transcription initiation site and the 5' transcribed noncoding region from an HSV γ gene. Synthetic promoters of the invention that are operatively linked to heterologous genes, inserted into HSV genomes and used to generate live virus are useful for expressing polypeptides encoded by the heterologous genes in appropriate host cells. The synthetic promoters direct transcription of the heterologous genes constitutively throughout the reproductive cycle of the virus at a high cumulative level. The recombinant viruses of the invention can also be used as vaccines to present polypeptides against which a host will mount an immune response.

10 Claims, 7 Drawing Sheets

| VIRUS | PLASMID | SEQUENCE ARRANGEMENT |
|---|---|---|
| R7600 | pRB4303 | α4 / U$_L$19 / OVA.  −502  −12/−11  +189 |
| R7610 | pRB4220 | gC / OVA.  −2700  +137 |
| R3213 | pRB3213 | α4 / OVA.  −1467  +33 |

α 4 PROMOTER

γ 1 ICP5 PROMOTER

α/γ CHIMERIC PROMOTER

5,714,153

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GCCTGGGGGG  CGGCGGGGGG  CCGGCGGCCT  CCGCTGCTCC  TCCTTCCCGG  CGGCCGCTGG      60

GACTATATGA  GCCCGAGGAT  CC                                                  82
```

( 2 ) INFORMATION FOR SEQ ID NO:2:

( i ) SEQUENCE CHARACTERISTICS:
        ( A ) LENGTH: 797 base pairs
        ( B ) TYPE: nucleic acid
        ( C ) STRANDEDNESS: single
        ( D ) TOPOLOGY: linear ( i i ) MOLECULE TYPE: DNA -continued ( x i ) SEQUENCE DESCRIPTION: SEQ ID NO:2:

```
CGCCAGTGCT CGCACTTCGC CCTAATAATA TATATATATT GGGACGAAGT GCGAACGCTT      60
CGCGTTCTCA CTTCTTTTAC CCGGCGGCCC CGCCCCCTTG GGGCGGTCCC GCCCGCCGGC     120
CAATGGGGGG GCGGCAAGGC GGGCGGCCCT TGGGCCGCCC GCCGTCCCGT TGGTCCCGGC     180
GTCCGGCGGG CGGGACCGGG GGGCCCGGGG ACGGCCAACG GGCGCGCGGG GCTCGTATCT     240
CATTACCGCC GAACCGGGAA GTCGGGGCCC GGGCCCCGCC CCCGGCCCGT TCCTCGTTAG     300
CATGCGGAAC GGAAGCGGAA ACCACCGGAT CGGGCGGTAA TGAGATGCCA TGCGGGGCGG     360
GGCGCGGGCC CACCCGCCCT CGCGCCCCGC CCATGGCAGA TGGCGCGGAT GGGCGGGCCC     420
GGGGGTTCGA CCAACGGGCC GCGGCCACGG GCCCCGGCG TGCCGGCGTC GGGGCGGGGT     480
CGTGCATAAT GGAATTCCGT TCGGGCGGG CCCGCCTGGG GGGCGGCGGG GGGCGGCGG     540
CCTCCGCTGC TCCTCCTTCC CGGCGGCCGC TGGAACTATA TGAGCCGAG GATCCCACGT     600
CCCCGGGGTC TGTTGGGGAC ACTGGGTTCT CCTGGAACGA GGCCGCAGCC TTCTCCCGGT     660
GCCTTTCCCC CCCGACCGAC ACCCGGCCTC TCACACAGCA TCCCCCGCCT CTTTGGGTCC     720
GGGTCCGTCG TGTCGTCTTT CGGTGGACCT TGGGCCGTCG GGCACGTACA CGGGTGGCCG     780
GGCGTTGGGG TGGATCC                                                    797
```

( 2 ) INFORMATION FOR SEQ ID NO:3:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

```
GATCTTTATT AGGTACCCTC TAGAATAAAG AGCTAAATAA TCCATGGGAG ATCTTATTTC      60
```

1

METHOD OF INDUCING ANTIBODY PRODUCTION AGAINST AN INFECTIOUS AGENT IN A HOST

CROSS-REFERENCE TO RELATED APPLICATIONS

This application is a continuation of U.S. patent application Ser. No. 08/332,467 filed Oct. 31, 1994, now U.S. Pat. No. 5,641,651, which is a continuation of U.S. patent application Ser. No. 07/996,961 filed Dec. 23, 1992, now abandoned.

ACKNOWLEDGMENT OF GOVERNMENT SUPPORT

This invention was made with government support under Grant No. USPHS R35 CA47451 awarded by the National Institutes of Health. The government has certain rights in the invention.

FIELD OF THE INVENTION

The present invention relates generally to synthetic herpes simplex virus (HSV) promoters useful for expressing heterologous genes within the context of the HSV genome. More specifically, the invention relates to a synthetic viral promoter including the 5' nontranscribed domain of an HSV α gene operatively linked to the transcription initiation site and 5' transcribed non-coding domain of an HSV γ gene.

BACKGROUND

The HSV-1 genome includes at least seventy-six open reading frames which encode at least seventy-three diverse polypeptides. The genes encoded by the viral genome have been classified into three major groups designated as α, β and γ, whose expression is coordinately regulated and sequentially ordered in a cascade fashion. The α genes are expressed in the absence of prior viral protein synthesis. Expression of the α genes is induced by the interaction of an HSV structural protein designated as α-transinducing factor or virion protein No. 16 and several host proteins which interact with a response element located in the 5' untranscribed domains of all α genes. The products of the α genes trans-activate the expression of the β genes by a mechanism as yet unknown, but the response elements for the induction of the β genes appear to reside in their 5' untranscribed domains. Among the response elements commonly associated with β gene promoters are TATAA boxes, SP1 binding sites, CCAAT boxes, and sites for binding of the α4 gene product. The expression of γ genes also requires the expression of α genes. In addition, their expression is partially (the $\gamma_1$ genes) or totally (the $\gamma_2$ genes) dependent on viral DNA synthesis. In contrast to the α and β genes, in γ genes promoter response elements (including α4 protein binding sites) have been reported to be present in both 5' untranscribed and transcribed non-coding domains.

Various HSV promoters have been utilized to express non-HSV genes in the context of the HSV genome. Post et al., *Mol. Cell. Biol.*, 2:233-240 (1982) reports the expression of ovalbumin from a fusion of a chicken ovalbumin gene to the promoter of the α4 gene. Similarly, Hummel et al., *Virology*, 148:337-343 (1986) describes the expression of an Epstein-Barr virus protein, the EBNA1 protein, from the α4 promoter in the HSV genome. Synthetic genes consisting of the coding sequences of a foreign gene fused to a specific HSV promoter and inserted into the HSV genome are expressed in the temporal class of the promoter as is

2 reported, for example, in Shih et al., *Proc. Natl. Acad. Sci. USA*, 81:5867-5870 (1984) where the hepatitis B virus S gene specifying the hepatitis B virus surface antigen was inserted into the HSV genome under the control of the HSV α4 gene promoter and separately under the control of the HSV thymidine kinase gene β promoter.

While the HSV genome has been successfully utilized to express products of heterologous genes, inserting foreign genes under the control of native HSV promoters is problematic because of the sequential order of activation of HSV promoters. A foreign gene under the control of an HSV α promoter is transcribed early in the replicative process of the virus while a foreign gene under the control of an HSV γ promoter is transcribed only in the later stages of replication. Heterologous polypeptides or proteins are therefore not continuously expressed throughout the infection cycle of the virus and the potential level of foreign protein synthesized is correspondingly reduced.

There thus continues to be a need in the art for HSV synthetic promoters specifically designed to express gene products throughout the infectious process of the virus and overproduce the gene product.

SUMMARY OF THE INVENTION

The present invention provides synthetic HSV promoters that include an HSV (i.e., HSV-1 or HSV-2) α gene promoter fragment operatively linked 5' to an HSV (i.e., HSV-1 or HSV-2) γ gene promoter fragment. Also provided are DNA constructs including a synthetic HSV promoter of the invention operatively linked 5' to a heterologous gene, recombinant HSV genomes containing such DNA constructs, and recombinant viruses having such a recombinant HSV genomes.

The HSV α gene promoter fragment of the synthetic promoters of the invention consists essentially of the 5' nontranscribed domain of an α gene. The α gene promoter fragment preferably includes the promoter sequences upstream of the translation initiation site (i.e., cap site) and preferably is a fragment of the α4 gene. More preferably, the α4 gene promoter fragment consists essentially of nucleotides −588 to −12 of the α4 gene promoter relative to its transcription initiation site or of a functionally equivalent nucleotide sequence.

The HSV γ gene promoter fragment of the synthetic promoters of the invention consists essentially of the transcription initiation site and 5' transcribed non-coding domain of a γ gene. The γ gene fragment preferably includes the transcription initiation site and promoter sequences downstream of the transcription initiation site and preferably is a fragment of the $\gamma_1 U_L 19$ gene. More preferably, the $\gamma_1 U_L 19$ gene promoter fragment consists essentially of nucleotides −11 to +189 of the $\gamma_1 U_L 19$ gene promoter relative to its transcription initiation site or of a functionally equivalent nucleotide sequence.

Specifically illustrating synthetic HSV promoters of the invention is the synthetic promoter designated the α4-$\gamma_1 U_L 19$ promoter which was deposited in the plasmid pRB4297 in *E. coli* strain XL1 Blue with the American Type Culture Collection (ATCC), 12301 Parklawn Drive, Rockville, Md. 20852 on Sep. 4, 1992 and was assigned ATCC Accession No. 69068.

The synthetic promoter/heterologous gene DNA constructs of the invention when included in recombinant HSV genomes and/or recombinant viruses are useful for expressing heterologous polypeptides in appropriately transfected or infected host cells. (See Roizman, European Patent No.

176,170 granted on Aug. 19, 1992 which is directed to the use of herpes simplex virus as a vector.) The heterologous genes may encode any non-HSV polypeptide or protein of interest that confers immunity to infection, for example, surface glycoproteins of Epstein-Barr virus, influenza virus, human immunodeficiency virus, papilloma viruses, varicella-zoster virus, human cytomegalovirus and human herpesvirus HHV-6, as well as HSV proteins not naturally under the transcriptional control of either of the component promoters of the synthetic constructs. Transcription in a host cell from a synthetic promoter of the invention occurs constitutively throughout HSV infection and results in overproduction of the gene product. Specifically illustrating recombinant herpes simplex viruses of the invention is the recombinant herpes simplex virus R7125 which was deposited with the ATCC on Nov. 19, 1992 and was assigned ATCC Accession No. VR 2389.

The recombinant viruses described herein that include a heterologous gene operatively linked to a synthetic promoter of the invention are useful as vaccines. A host (especially a human host) may be immunized against a polypeptide of a disease-causing organism by administering to the host an immunity-inducing amount of a recombinant virus of the invention which produces the polypeptide. Immunization against polypeptides encoded by various non-HSV viruses and bacteria is contemplated, including Epstein-Barr virus (EBV), varicella-zoster virus and cytomegalovirus, as well as immunization against various other human herpesviruses. Herpes simplex viruses that are appropriate for insertion of the DNA constructs of the invention and for use as vaccines are avirulent strains (e.g., the strains described in Roizman, U.S. Pat. No. 4,859,587 issued on Aug. 22, 1989 and in Roizman, PCT International Publication No. WO 92/04050 published on Mar. 19, 1992).

Immunization of a human host with a recombinant herpes simplex virus of the invention involves administration by inoculation of an immunity-inducing dose of the virus by the parenteral route, preferably by intramuscular or subcutaneous injection. Inoculation may also by effected by surface scarification or by inoculation into a body cavity. Typically, one or several inoculations of between about 1000 and about 10,000,000 plaque-forming units each, as measured in susceptible human or nonhuman primate cell lines, are sufficient to effect immunization of a human host. Virus to be used as a vaccine may be utilized in liquid or freeze-dried form (in combination with one or more suitable preservatives and/or protective agents to protect the virus during the freeze-drying process).

DETAILED DESCRIPTION

The following detailed description illustrates practice of the invention in the context of a single illustrative synthetic promoter whose design is based on the observation that the response elements for transactivators of HSV $\alpha$ genes are located upstream of the transcription initiation site whereas $\gamma$ gene response elements are found downstream of the transcription initiation site. Construction of the synthetic promoter thus takes advantage of the hitherto unrecognized prospect that the 5' untranscribed domain of an $\alpha$ gene, when fused to the 5' transcribed non-coding domain of a $\gamma$ gene, forms a promoter that expresses a gene product throughout HSV infection and overproduces the gene product.

The HSV-1 $\alpha$ promoter fragment selected for illustration here consists of the nucleotides −588 to −12 of the $\alpha 4$ promoter relative to its transcription initiation site. This sequence includes several $\alpha$-TIF response elements, several SP1 binding sites, and the native $\alpha 4$ TATAA box. For the $\gamma$ promoter fragment, a domain of the $\gamma_1 U_L 19$ gene consisting of nucleotides −11 to +189 relative to its transcription initiation site was selected. The $U_L 19$ gene encodes virion protein VP5, the major capsid protein of the virus. Previous studies [see Honess et al., *J. Virol.*, 14:8–19 (1974); Honess et al., *Proc. Natl. Acad. Sci. USA*, 72:1276–1280 (1975); and Roizman et al., Eds., *The Herpesviruses*, Vol. 3, Plenum Press, New York, 45–104 (1984)] report that VP5 is an abundant protein whose synthesis is only partially affected by inhibitors of DNA synthesis.

Numerous aspects and advantages of the present invention will be apparent upon consideration of the following examples relating to the construction and use of synthetic herpes virus promoters. More particularly, Example 1 describes the construction of the synthetic $\alpha 4$-$\gamma_1 U_L 19$ promoter, fusion of the synthetic promoter to a chicken ovalbumin gene in a recombinant HSV-1 genome, and generation of a recombinant virus, designated R7600, therefrom. Example 2 describes the testing of recombinant virus R7600 for the capacity to produce ovalbumin and an analysis of the production of ovalbumin by the recombinant virus during infection of host cells in comparison to control viruses. Example 3 describes the construction of a DNA construct including the synthetic $\alpha 4$-$\gamma_1 U_L 19$ promoter fused to structural sequences encoding the Epstein Barr virus glycoprotein gp350/220 and the generation of a recombinant virus, desginated R7125, having the DNA construct within its genome. Example 4 describes the testing of recombinant virus R7125 for the capacity to produce gp350/220 in comparison to a control virus and the stability of the recombinant virus after serial passage.

EXAMPLE 1

Figures 1, 2:
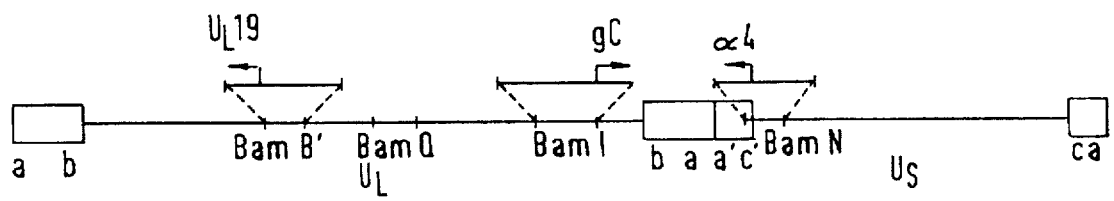
FIG. 1 is a schematic representation of the HSV-1 genome and the natural locations of the promoters used in the construction of an $\alpha_4$-$\gamma_1 U_L 19$ promoter of the invention.
FIG. 2 is a schematic representation of the structure of three synthetic HSV promoter DNA constructs respectively included in recombinant viruses R3213, R7610 and R7600.

FIG. 1 schematically depicts the HSV-1 genome and the locations of restriction fragments of the genome which contain the promoter fragments of the HSV-1 $U_L 19$, $U_L 44$ (or gC) and α4 genes utilized herein. In FIG. 1, ab and b'a' represent the inverted repeats flanking the $U_L$ components, whereas a'c' and ca represent the inverted repeats flanking the $U_s$ component. The locations of BamHI fragments B', I and N which respectively contain the $U_L19$, gC and of α4 promoters are indicated.

A synthetic HSV promoter, designated the α4-$\gamma_1U_L19$ promoter, was constructed as follows. DNA of bacterial plasmid clone pRB140 [Post et al., Proc. Natl. Acad. Sci. USA, 77:4201–4205 (1980)], which contains the BamHI B' fragment of the wild type HSV-1(F) strain (ATCC VR 733) including portions of the promoter of the $U_L19$ gene, was subjected to digestion with restriction enzymes BamHI and SalI. The resulting ~1074 base pair (bp) fragment was ligated into the vector pGEM3z (Promega, Madison, Wis.) which had been digested with BamHI and SalI to yield pRB4291. DNA from pRB4291 was then digested with BamHI and BstYI, and the 200 bp fragment which resulted was ligated into pGEM3z digested with BamHI to create pRB4294. This clone contains five tandem copies of the fragment representing the region −11 to +188 of the $U_L19$ promoter relative to the transcriptional start site of the $U_L19$ RNA.

A second plasmid, pRB4295, containing promoter elements of the α4 gene was derived from pRB168 (Post et al., supra) which contains the BamHI fragment Z of HSV-1(F). Plasmid pRB168 DNA was digested with NarI and BglI and a 420 bp fragment was isolated and ligated to a synthetic double stranded oligonucleotide (the sequence of which is set out below) which conforms in part to elements from −88 to −12 in the α4 promoter region (see description of pRB4295 below for differences).

SEQ ID NO: 1
GC CTG GGG GGC GGC GGG GGG CCG GCG GCC TCC GCT
GCT CCT CCT TCC C<u>GG CGG CCG</u> CTG GGA CTA TAT GAG
CCC GAG <u>GAT CC</u>

The ligation product was redigested with NarI to uncouple fragments which had been ligated in tandem at the −520 NarI site. After repurification, the appropriate 500 bp product was ligated into pGEM3z which had been digested with AccI and BamHI to yield pRB4295. pRB4295 contains the natural α4 promoter elements from −520 to −88, natural sequence restored by the oligonucleotide from −88 to −40, then two nucleotide base changes to introduce a NotI recognition site (underlined). Natural sequences are restored from −37 through the natural TATA element at −28 (bold) to an induced BamHI recognition site at −12 (double underlined).

A 200 bp fragment containing a portion of the 5' untranscribed sequence, the transcription initiation site and the 5' transcribed non-coding sequence of the $\gamma_1U_L19$ gene (i.e., the transcription initiation site and sequences downstream of the transcription inflation site of the $\gamma_1U_L19$ gene) was excised from pRB4294 with BamHI and inserted into the induced BamHI site of pRB4295, such that base −11 of the $\gamma_1U_L19$ fragment was adjacent to base −12 of the α4 promoter to generate the plasmid designated pRB4297 (ATCC 69068). The DNA sequence of the synthetic α4-$\gamma_1U_L19$ promoter is set out in SEQ ID NO: 2, wherein nucleotides 1 to 594 correspond to the α4 gene promoter fragment, nucleotides 595 to 797 correspond to the $\gamma_1U_L19$ gene promoter fragment, and nucleotide 606 is the transcription start site.

Plasmid pRB4297 was digested with KpnI and HindIII and the resulting 700 base pair fragment containing the α4-$\gamma_1U_L19$ synthetic promoter was inserted into the KpnI site of pRB4302 to generate plasmid pRB4303. pRB4302 contains an entire HSV-1 genome with a cDNA copy of the structural sequences of the chicken ovalbumin gene inserted into the BglII site in the leader of the thymidine kinase (tk) gene of the HSV-1 Bam Q fragment (see FIG. 1). The KpnI site of pRB4302 is adjacent to the translational start site of the chicken ovalbumin gene. The orientation in which the synthetic α4-$\gamma_1U_L19$ promoter was inserted into pRB4303 was the correct transcriptional orientation with respect to the translation start site of the ovalbumin gene. A schematic representation of the synthetic HSV promoter/ovalbumin gene DNA construct in pRB4303 is set out in FIG. 2, wherein the wide box labeled "ova" represents the cDNA sequence of the structural portion of the chicken ovalbumin gene, the thin boxes represent the promoter regions and the arrowhead denotes the transcriptional orientation of the promoter.

The synthetic HSV promoter/ovalbumin DNA construct was inserted into an HSV-1 genome by recombination through thymidine kinase sequences flanking the DNA construct by a method similar to that described in Post et al., Cell, 25: 555–565 (1981). Specifically, cotransfection of rabbit skin cells with DNA from pRB4303 and with DNA from the wild type HSV-1 strain HSV(F), followed by selection on 143TK cells for the TK$^+$ phenotype produced a number of recombinant viruses which then were plaque purified twice on Vero cells. DNA was isolated from each recombinant virus, digested with KpnI, and checked by Southern blot analysis for a change in the electrophoretic mobility of the Kpn fragment which would indicate the acquisition of pRB4303 sequences containing the synthetic HSV promoter/ovalbumin construct. Of the fourteen recombinant viruses tested, five contained the α4-$\gamma_1U_L19$ synthetic promoter/chicken ovalbumin gene construct.

EXAMPLE 2

The five recombinant viruses generated in Example 1 were tested for the capacity to produce chicken ovalbumin. By a method described in Arsenakis et al., Methods in Molecular and Cellular Biology, 2:5–16 (1990), all five were shown to produce comparable amounts of ovalbumin when the extracellular medium of infected cells was electrophoresed in denaturing polyacrylamide gels. One of these five viruses, designated R7600, was chosen for temporal analysis of ovalbumin expression during the HSV infection cycle by detection of the protein excreted from infected cells by immunoprecipitation with commercially available anti-ovalbumin antibody.

HSV-1(F) and two different HSV-1 recombinant viruses were used as controls in the experiments. The first recombinant virus, R3213, contains the nucleotides −1467 to +33 of the α4 promoter fused to the chicken ovalbumin gene and inserted into the BglII site of the tk gene in the HSV-1 genome as present in intermediate plasmid pRB3213. See Arsenakis et al., supra, and FIG. 2. The second, R7610, contains nucleotides −2700 to +137 of the promoter of the HSV glycoprotein C gene ($U_L44$) fused to the chicken ovalbumin gene and similarly inserted into the HSV genome. See FIG. 2. Like the product of the $U_L19$ gene, the product of the $U_L44$ gene is made in abundant mounts. The R7600 virus of the invention and the three control viruses were propagated on HEp-2 cells and titered on Vero cells.

Figure 3:
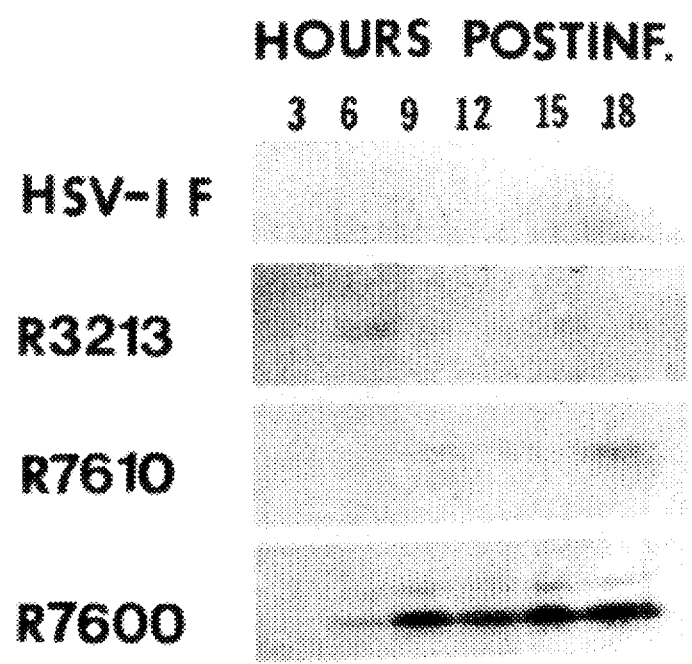
FIG. 3 is an autoradiographic image of chicken ovalbumin immunoprecipitated from the extracellular medium of cells respectively infected with HSV-1(F) (wild type HSV) and recombinant viruses R3213, R7610 and R7600.
Figure 4:
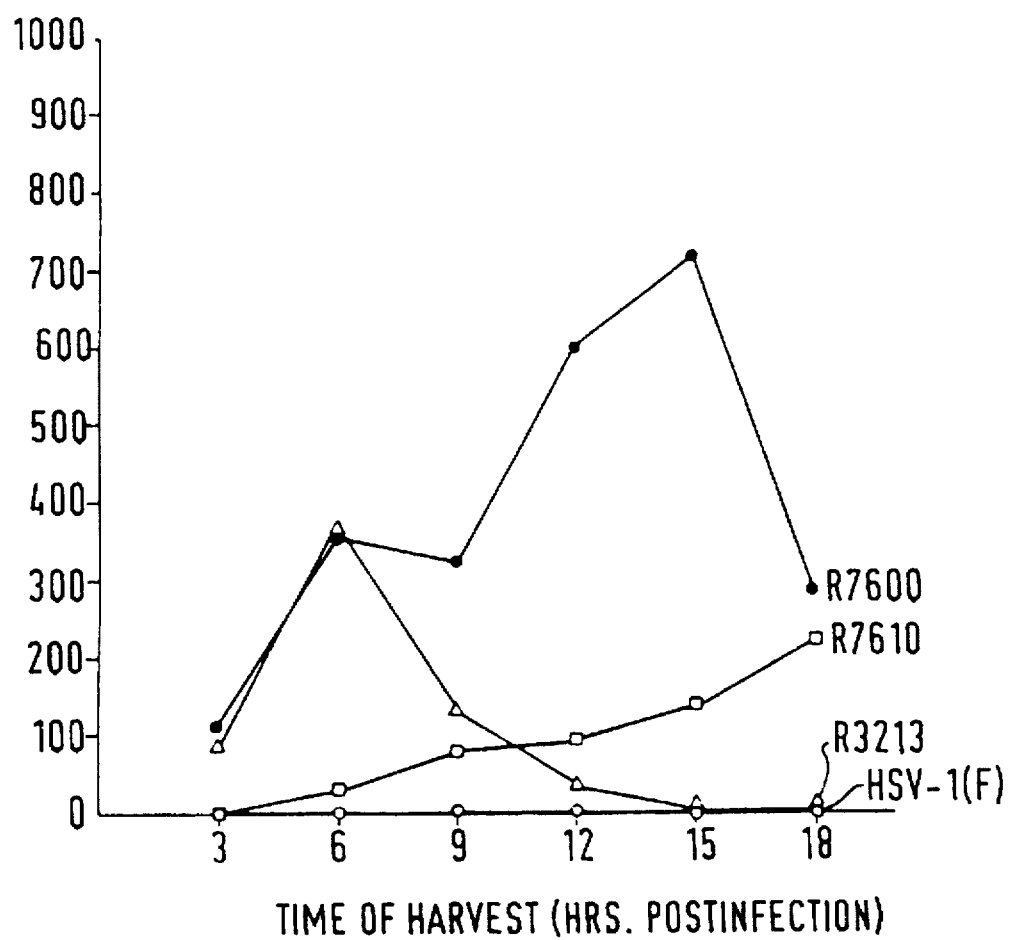
FIG. 4 is a graph depicting the relative amounts of chicken ovalbumin made in cells during infection with HSV-1(F) and recombinant viruses R3213, R7610 and R7600.

Replicate cultures of HEp-2 cells were each infected with 10 plaque-forming units (pfu) of HSV(F), R7600, R3213 or R7610 viruses. At 2, 5, 8, 11, 14, and 17 hours post infection, the medium was replaced with 1 ml of 199V (JRH Bioscience, Lenexa, Kans.) without calf serum. ⅒ the normal concentration of methionine, and 100 µCi of $^{35}$S-methionine (>1000 Ci/mmol; Amersham, Arlington Heights, Ill.). One hour later the medium was collected, clarified by centrifugation, and concentrated 10-fold. Chicken ovalbumin was then collected from each sample by immunoprecipitation with anti-chicken ovalbumin antibody (Organon Teknika, West Chester, Pa.) and Protein A conjugated sepharose beads (Sigma Chemical Co., St. Louis, Mo.). The ovalbumin was eluted from the beads with disruption buffer containing sodium dodecyl sulfate, electrophoretically separated on a 9.5% denaturing polyacrylamide gel, electrically transferred onto a nitrocellulose sheet (Scheicher and Schuell, Keene, N.H.) and visualized by its reactivity with antibody, autoradiography, or both. In some experiments the amount of labeled $^{35}$S-methionine labeled ovalbumin was quantified with a Betascope 603 (Betagen, Waltham, Mass.). An example of the results obtained by these procedures is an autoradiogram presented in FIG. 3. Similar results are presented graphically in FIG. 4.

The timing and level of chicken ovalbumin expression in R7600-infected cells during early infection were nearly identical to that observed in R3213-infected cells (because the ovalbumin gene is under the control of an $\alpha$ promoter in the R3213 virus). At 9 hours post infection, when production was decreasing in R3213-infected cells, the level from R7600-infected cells stabilized. After 9 hours, the level of ovalbumin from R3213-infected cells declined until no ovalbumin was detectable, while the level from R7600-infected cells increased dramatically. This increase occurred at approximately the time in HSV infection that expression switches from the $\alpha$ and $\beta$ genes to the $\gamma$ genes. The amount of chicken ovalbumin produced by R7600-infected cells during the late phase of the infection was much greater than that from R7610-infected cells even though the ovalbumin gene was under the control of a $\gamma$ promoter in the R7610 virus.

Over the course of viral infection, the yield of chicken ovalbumin from R7600-infected cells was at least 57-fold greater than the background measured in the medium of cells infected with HSV(F), 5.2-fold more than produced by R7610-infected cells, and 3.8-fold more than in cells infected with R3213.

EXAMPLE 3

Epstein-Barr virus (EBV) infects and predominantly remains latent in human B lymphocytes. The virus is mainly associated with subclinical infection, but primary infection with EBV is the cause of infectious mononucleosis. Recent interest has focused on EBV because it may play a role as a human carcinogenic agent in the etiology of Burkitt's lymphoma and nasopharyngeal carcinoma. Immunization against EBV is thus indicated for individuals susceptible to or infected with the virus.

Figure 5:
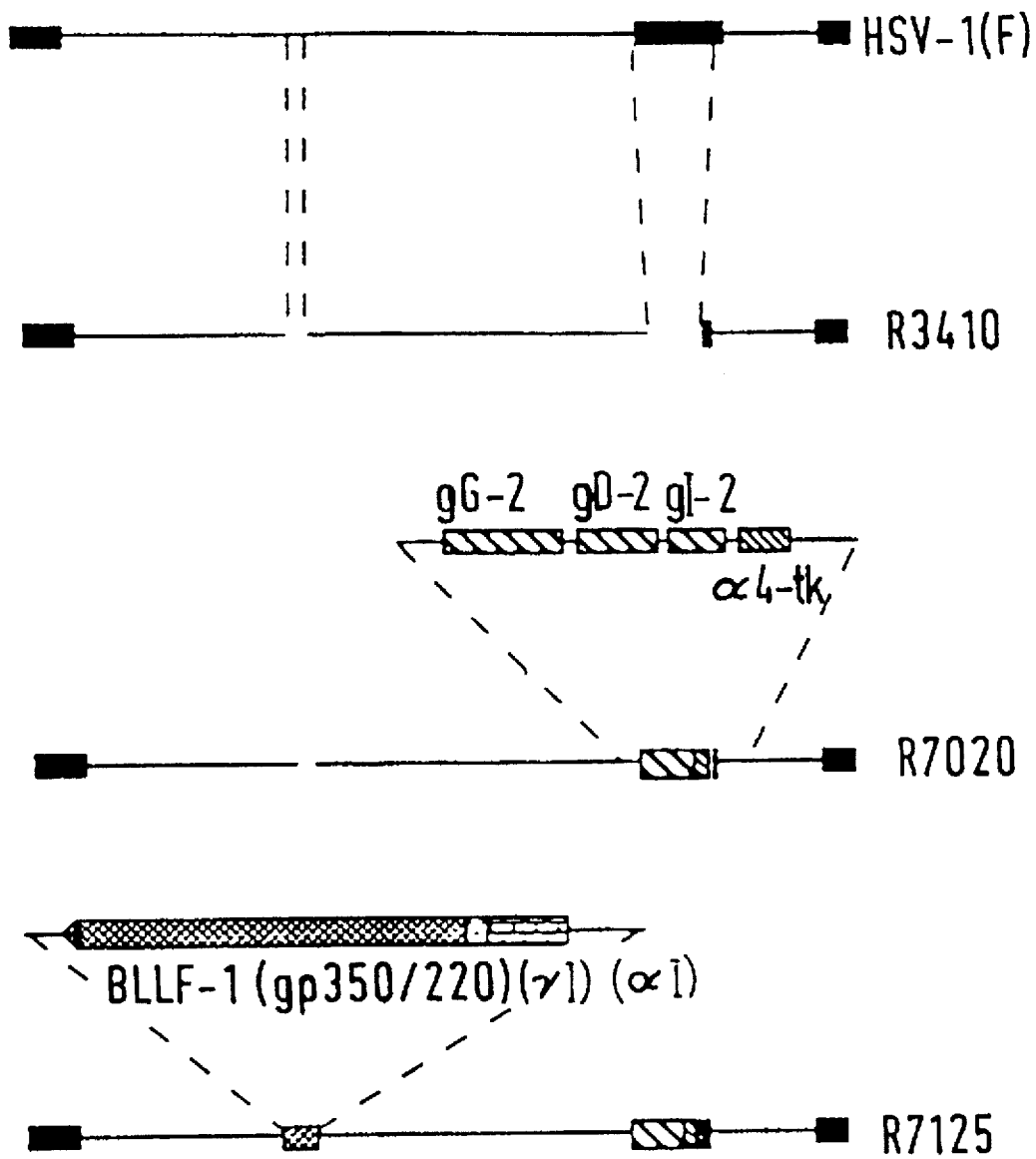
FIG. 5 is a schematic representation of the genomes of HSV-1(F) and of recombinant viruses R3410, R7020 and R7125.

The synthetic $\alpha 4$-$\gamma_1 U_L 19$ HSV promoter described in Example 1 was fused to an EBV gene encoding the viral glycoprotein gp350/220. A recombinant virus, designated R7125, having the synthetic HSV promoter/gp350/220 synthetic gene as part of its genome was derived from a stable genetically engineered attenuated strain of HSV-1 designated R7020 (ATCC VR2123). See Meignier et al., J. Infect. Dis., 158:602–614 (1988)and Meignier et al., J. Infect. Dis., 162:313–322 (1990). See also FIG. 5 wherein line 1 represents the genotype of wild type HSV(F); line 2 indicates the deletions present in R3410 (ATCC VR2124) to attenuate the virus (R3410 has deletions in the tk, $U_L 24$, $U_L 55$, $U_L 56$ genes and only has single copies of $\alpha 4$, $\alpha 0$, and $\gamma 34.5$ genes and the latency associated transcript sequence); line 3 depicts the addition of three glycoprotein genes from HSV-2(G) (ATCC VR734) and of an $\alpha 4$ promoter driven tk gene (in a nonnatural site) to R3410 to create R7020 (R7020 expresses gG-2, gD-2, gI-2 and $\alpha$tk); and the fourth line shows the introduction of the synthetically driven gp350/220 into the locale of the deleted site of tk and $U_L 24$ in R7125.

To link the EBV gp350/220 coding sequences to the $\alpha 4$-$\gamma_1 U_L 19$ promoter, pRB4297 (the plasmid described in Example 1 which contains the $\alpha 4$-$\gamma_1 U_L 19$ synthetic promoter) was cut with KpnI and HindIII to generate a fragment including the promoter. The sticky ends of the fragment were blunt-ended with T4 DNA polymerase and deoxynucleotides, and the fragment was ligated to the DNA of clone pMA102 (containing the BLLF-1 gene of EBV which encodes gp350/220) that had been digested with XbaI and BamHI and blunt-ended. The resulting plasmid, pRB4298, has the EBV gp350/220 coding sequences at −220 relative to the transcriptional start site of the synthetic promoter. pRB4298 was partially sequenced at the 5' end of the $\alpha 4$ portion of the synthetic promoter to verify orientation.

To provide flanking homologous sequences to allow recombination of the synthetic $\alpha 4$-$\gamma_1 U_L 19$ promoter/gp350/220 DNA construct into the genome of R7020, a plasmid was constructed as a shuttle vector which contained a genomic deletion identical to the deletion in the natural viral thymidine kinase gene of R7020 and which had a suitable polylinker for cloning other genetic elements. pRB173 (Post et al., supra) which contains the BamHI Q segment of HSV(F) in pUC9 was digested with BglII and SacI to delete 500 bp of the sequences of $U_L 23$ and $U_L 24$, the identical deletion present in R7020. Into the plasmid was introduced a double stranded synthetic oligonucleotide having the following top strand sequence:

SEQ ID NO: 3
GAT CTT TAT TAG GTA CCC TCT AGA ATA AAG
AGC TAA ATA ATC CAT GGG AGA TCT TAT TTC

The introduction of the oligonucleotide restored the BglII and SacI restriction sites, induced restriction sites for KpnI and XbaI (which are not otherwise present in the pUC9 vector) and produced bidirectional polyadenylation signals. The resulting shuttle vector was designated pRB3982.

Figure 6:
FIG. 6 is a schematic representation of the synthetic HSV promoter/Epstein Barr virus glycoprotein gp350/220 DNA construct in recombinant virus R7125.
Figure 6:
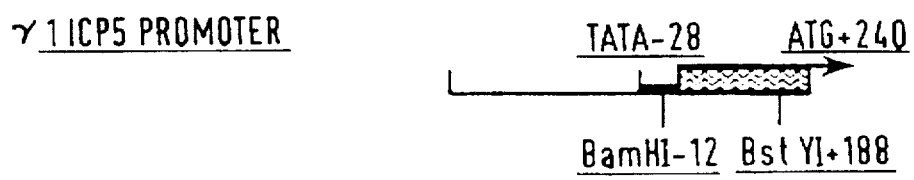
Figure 6:
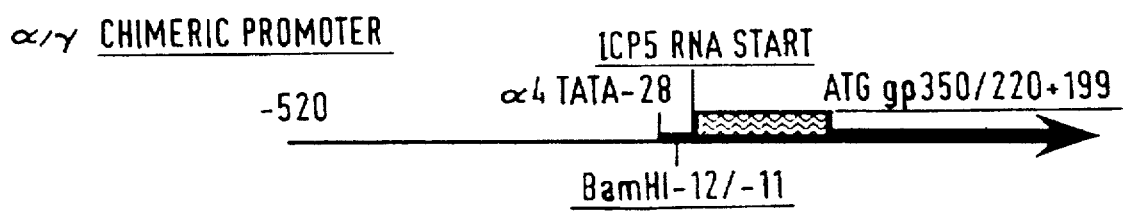
Figure 6:
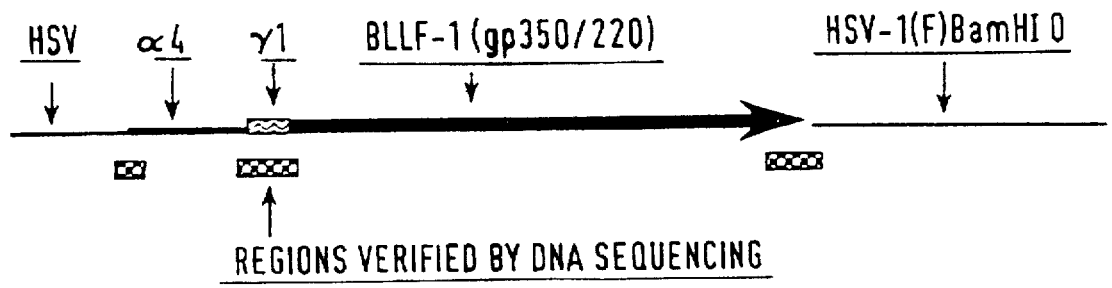

A 3000 bp fragment of pRB4298 containing the synthetic $\alpha 4$-$\gamma_1 U_L 19$ promoter/gp350/220 DNA construct was obtained by digestion with KpnI and HincII. The fragment was ligated into the shuttle vector pRB3982 which had been digested with XbaI, treated with T4 polymerase and deoxynucleotides, and then cut with KpnI. The resulting plasmid, pRB4299, contains the natural polyadenylation and transcriptional termination signals of the gp350/220 gene at the 3' terminus of the synthetic $\alpha$-$\gamma$ promoter/gp350/220 DNA construct. The synthetic promoter lies toward the truncated $U_L 24$ gene. FIG. 6 is a schematic representation of the construction wherein NarI, BamHI, BstVI denote restriction enzyme recognition sites; TATA denotes the critical transcriptional initiation signal; boxed regions indicate transcribed, nontranslated portions of the various promoters; ATG denotes the methionine codon at which translation is initiated; numbers indicate positions relative to the transcriptional initiation site of the native promoter; and boxed regions below the lines indicated regions which were verified by sequencing. The first line of FIG. 6 displays the features of the natural promoter of the $\alpha 4$ gene from pRB168. The γ1 ICP5 promoter in the second line is the natural promoter of the γU$_L$19 gene from pRB140. The third line indicates the arrangement of the synthetic promoter. The fourth line sets out the arrangement of the synthetic promoter attached to the gp350/220 gene flanked by homologous sequences derived from pRB3982 as present in pRB4299.

To obtain recombinant virus R7125 (ATCC VR 2389), vital DNA of R7020 and plasmid DNA of pRB4299 were cotransfected into rabbit skin cells by the method described in Example 1. Plaques were selected for expression of gp350/220 by treatment with anti-gp350/220 antibody followed by staining with immunoperoxidase. Complement free media was used after it was determined that the staining reaction resulted in complement activation and destruction of the recombinant virus infected cells. After 5 rounds of serial selection, R7125 was determined to be free of contaminating R7020 parent virus.

EXAMPLE 4

Recombinant virus R7125 was serially passaged in Vero cells seven times, and the passaged virus was analyzed with regard to its DNA restriction profile. The expression of gp350/220 by nonpassaged R7125 and passaged R7125 (R7125P7) in comparison to parent virus R7020 was also analyzed.

Figure 7A:
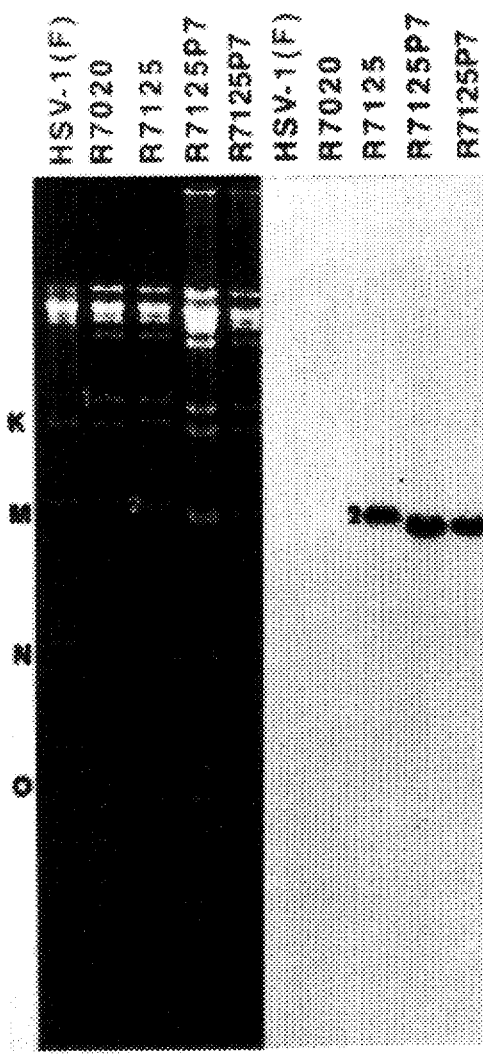
FIGS. 7A and 7B are autoradiographic images of HSV-1(F), recombinant virus R7020, nonpassaged recombinant virus R7125 and serially passaged R7125P7 DNA digested with EcoRI or EcoRV, respectively, and hybridized to DNA encoding Epstein Barr virus glycoprotein gp350/220.
Figure 7B:
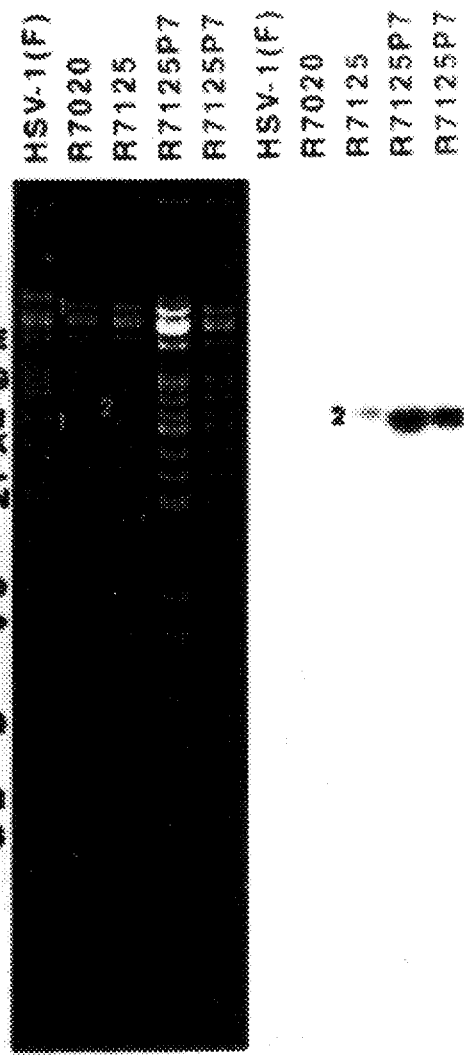

Stability of R7125 after serial passage was assessed by DNA hybridization. Viral DNA was digested with EcoRI or EcoRV, separated in 8% agarose in Tris-phosphate at 70 volts overnight, stained with ethidium bromide and photographed. DNA was then transferred by gravity and capillary action to nitrocellulose and hybridized with gp350/220 DNA which had been nick translated and radiolabelled with $^{32}$P-dCTP. Resulting bands are shown in FIGS. 7A (EcoRI) and 7B (EcoRV), wherein bands (denoted by the number 1) representing the added HSV-2 genes ("added" in comparison to R3410) in R7020 are demonstrated to be present in R7125 and unique bands in R7125 (denoted by the number 2) contain the ~3000bp synthetic α4-γ$_1$U$_L$19 promoter/gp350/220 insert which contains an EcoRI but not an EcoRV recognition site. The unique bands introduced by the added sequences in R7125 are stable in R7125.

Figure 8:
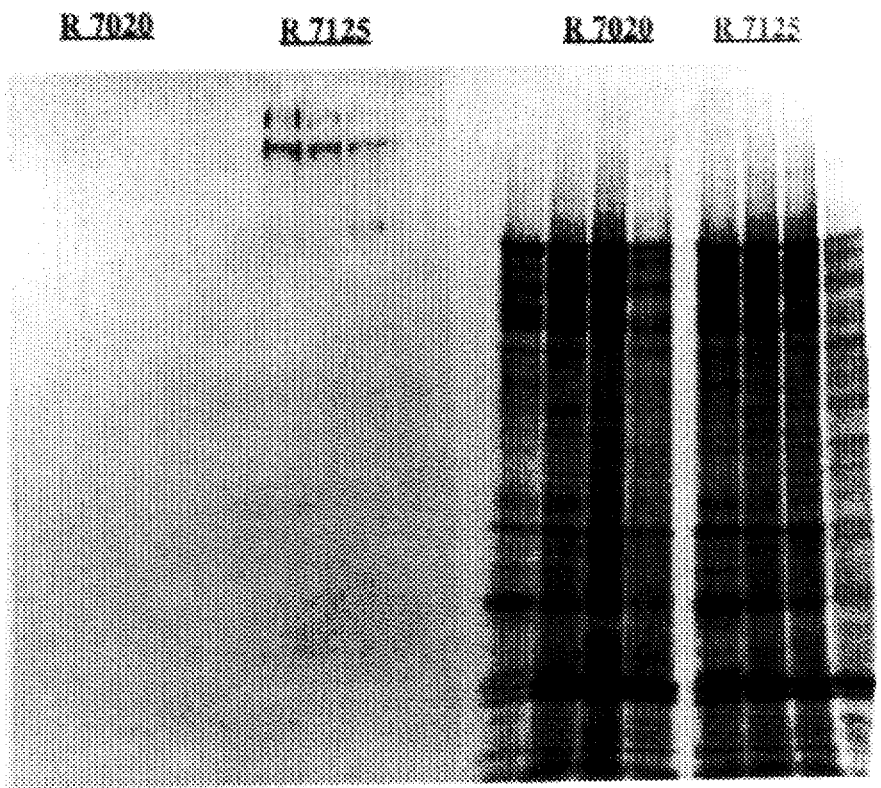
FIG. 8 is an autoradiographic image of gp350/220 immunoprecipitated from cells infected with recombinant virus R7020 and with recombinant virus R7125.

Recombinant viruses R7020 and R7125 were compared for expression of EBV gp350/220. Extracts of Vero cells (~4×10$^5$ cells) which were infected with 5 pfu virus were harvested at 2, 4, 6 and 14 hours post-infection after labelling with S$^{35}$-Met for the last hour before harvest. Extracts were electrophoresed in 5% bis-acrylamide gels then transferred to nitrocellulose and gp350/220 was detected by anti-gp350/220 monoclonal antibody followed by alkaline phosphatase conjugated goat anti-mouse antibody. Results of the assay are presented in FIG. 8. While R7020 extracts did not contain detectable gp350/220, expression of gp350/220 increased over time in R7125 extracts. The upper bands in the antibody-treated R7125 lanes of FIG. 8 represent authentic gp350 and spliced gp220 as occurs in EBV-infected lymphocytes, while the lower bands represent precursors to the glycosylated mature protein. Extracts of cells infected with a R7125P7 isolate contained similar quantities of gp350/220 when compared to extracts of cells infected with nonpassaged R7125. Kinetics of expression of gp350/220 by nonpassaged and passaged R7125 appear to be similar with large quantities appearing between 2 and 4 hours and continuing to 14 hours.

The foregoing illustrative examples relate to presently preferred embodiments of the invention and numerous modifications and variations thereof will be expected to occur to those in the art. Thus only such limitations as appear in the appended claims should be placed upon the scope of the present invention.

What is claimed is:

1. A method of inducing antibody production against a polypeptide from a disease-causing organism in a host, said method comprising the step of administering an antibody-inducing dose of a recombinant herpes simplex virus to said host, said recombinant herpes simplex virus comprising a recombinant herpes simplex virus genome comprising a synthetic herpes simplex virus promoter and a heterologous gene operatively linked 3' to said synthetic promoter, said synthetic promoter comprising a herpes simplex virus α gene promoter fragment operatively linked 5' to a herpes simplex virus γ gene promoter fragment, wherein said polypeptide is encoded by said heterologous gene, said heterologous gene being derived from said disease-causing organism.

2. The method of claim 1 wherein said herpes simplex virus α gene promoter fragment comprises promoter sequences upstream of the transcription initiation site of said α gene.

3. The method of claim 1 wherein said herpes simplex γ gene promoter fragment comprises the transcription initiation site and the transcribed non-coding sequences downstream of the transcription initiation site of said γ gene.

4. The method of claim 1 wherein said herpes simplex virus α gene promoter fragment comprises promoter sequences upstream of the transcription initiation site of the α4 gene and said herpes simplex virus γ gene promoter fragment comprises the transcription initiation site and the 5' transcribed non-coding sequences of the $\gamma_1 U_L 19$ gene.

5. The method of claim 1 wherein said heterologous gene encodes part or all of the Epstein-Barr virus glycoprotein gp 350/220.

6. The method of claim 1 wherein the recombinant herpes simplex virus is the virus deposited as ATCC VR 2389.

7. The method of claim 2 wherein said herpes simplex virus α gene promoter fragment is an α4 gene promoter fragment.

8. The method of claim 7 wherein said herpes α4 gene promoter fragment comprises nucleotides −588 to −12 of said α4 gene promoter.

9. The method of claim 3 wherein said herpes simplex virus γ gene promoter fragment is a $\gamma_1 U_L 19$ gene fragment.

10. The method of claim 9 wherein said herpes simplex virus $\gamma_1 U_L 19$ gene fragment comprises bases −11 to +189 of said $\gamma_1 U_L 19$ gene promoter.

* * * * *